(12) United States Patent
Khanna

(10) Patent No.: US 6,831,162 B2
(45) Date of Patent: Dec. 14, 2004

(54) **PROTEIN/POLYPEPTIDE-K OBTAINED FROM *MOMORDICA CHARANTIA* AND A PROCESS FOR THE EXTRACTION THEREOF**

(76) Inventor: Pushpa Khanna, E. 14/7, $1^{st}$ Floor, Vasant Vihar, New Delhi, 110 057 (IN)

(*) Notice: Subject to any disclaimer, the term of this patent is extended or adjusted under 35 U.S.C. 154(b) by 0 days.

(21) Appl. No.: 09/881,569

(22) Filed: Jun. 14, 2001

(65) Prior Publication Data

US 2002/0151687 A1 Oct. 17, 2002

Related U.S. Application Data

(63) Continuation-in-part of application No. PCT/IN99/00052, filed on Sep. 28, 1999.

(30) Foreign Application Priority Data

Apr. 13, 1999 (IN) ................................................ 560/99
Apr. 13, 1999 (IN) ................................................ 561/99

(51) Int. Cl.$^7$ ................................................ C07K 1/00
(52) U.S. Cl. ...................................................... 530/530
(58) Field of Search ................................ 530/350, 300, 530/370, 379; 514/2, 12, 21

(56) References Cited

PUBLICATIONS

Jeevathayaparan, S.; Tennekoon, Kamani H.; Karunanayake, Eric H.; Jayasinghe, K. S. A. Oral hypoglycaemic activity of different preparations of *Momordica charantia*. Journal of the National Science Council of Sri Lanka, (1991) vol. 19, No. 1, pp. 19–24.*

* cited by examiner

*Primary Examiner*—Karen Cochrane Carlson
*Assistant Examiner*—Sheridan K Snedden
(74) *Attorney, Agent, or Firm*—Ladas & Parry

(57) ABSTRACT

The invention relates to a novel and highly effective hypoglycemic protein called polypeptide-k, extracted from *Momordica charantia*, provides a method for the extraction of said polypeptide-k from *Momordica charantia* and provides novel hypoglycemic compositions employing the said extract, and useful in the treatment of diabetes mellitus.

1 Claim, 18 Drawing Sheets

CAMAG ILC Evaluation Software
****************************

ARBRO PHARMACEUTICALS LTD 6/14 KIRTI NAGAR INDUSTRIAL AREA NEW DELHI
PHONE: 5467228.515-0437. FAX: 91-11-5463784, E-mail: arbo@vsn1.com TLC/HPTLC-Integration (CATS3.18 S/N:0207A004 / SCANNER I I  V3.14 S/N:990602)

ESTIMATION OF L-LYSINE BY HPTLC

| Calibr. Table | Calibration Table created: | ARBRO PHARMA LTD | |
|---|---|---|---|
| | File name: AMINO | 3/JUN/ 0 | 14:49:46 |
| Scan | User name wnile measuring : | ARBRO PHARMA LTD | |
| | File name: AMINO | 3/JUN/ 0 | 14:54:52 |
| INTEGRATION | User while integrating: | ARBRO PHARMA LTD | |
| | File name: AMINO | 3/JUN/ 0 | 15:19:26 |

Track 1. Analysis a:

| Peak | start | | max | | | end | | area | |
|---|---|---|---|---|---|---|---|---|---|
| # | mm | h | mm | h | [%] | mm | h | a | [%] |
| 1 | 61.1 | 0.4 | 72.6 | 64.1 | 100.00 | 78.2 | 0.1 | 3186.2 | 100.00 |
| | Total height = | | | 64.1 | | Total area = | | 3186.2 | |

Track 2. Standard level 1:

| Peak | start | | max | | | end | | area | |
|---|---|---|---|---|---|---|---|---|---|
| # | mm | h | mm | h | [%] | mm | h | a | [%] |
| 1 | 62.9 | 2.8 | 71.0 | 63.5 | 100.00 | 78.8 | 0.0 | 3133.9 | 100.00 |
| | Total height = | | | 63.5 | | Total area = | | 3133.9 | |

FIG. 2A

Figure 2B:
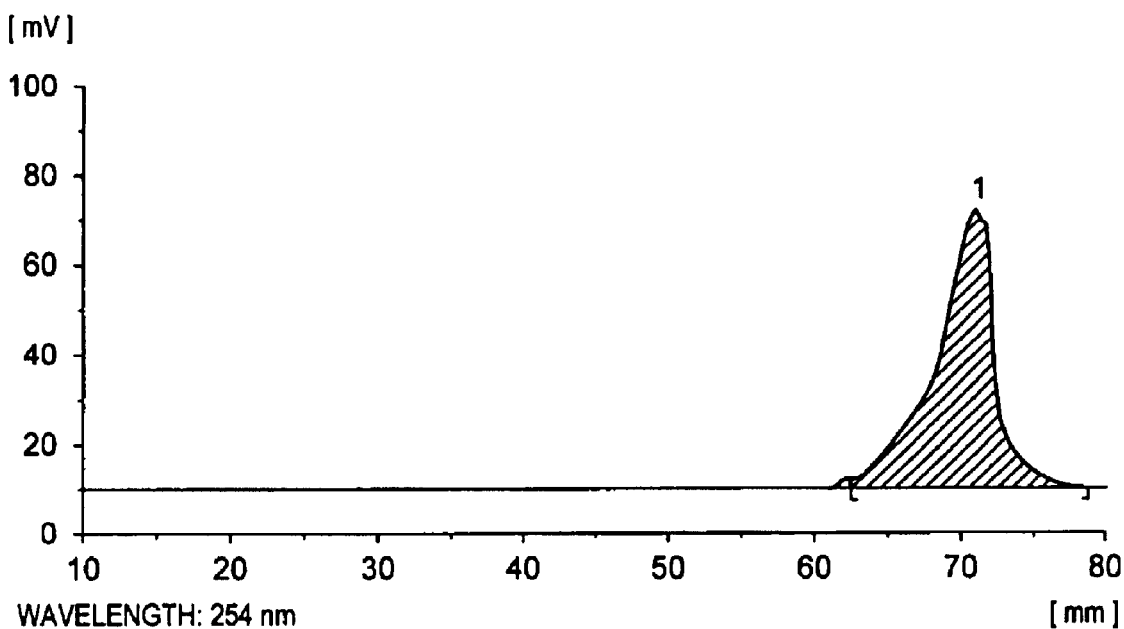

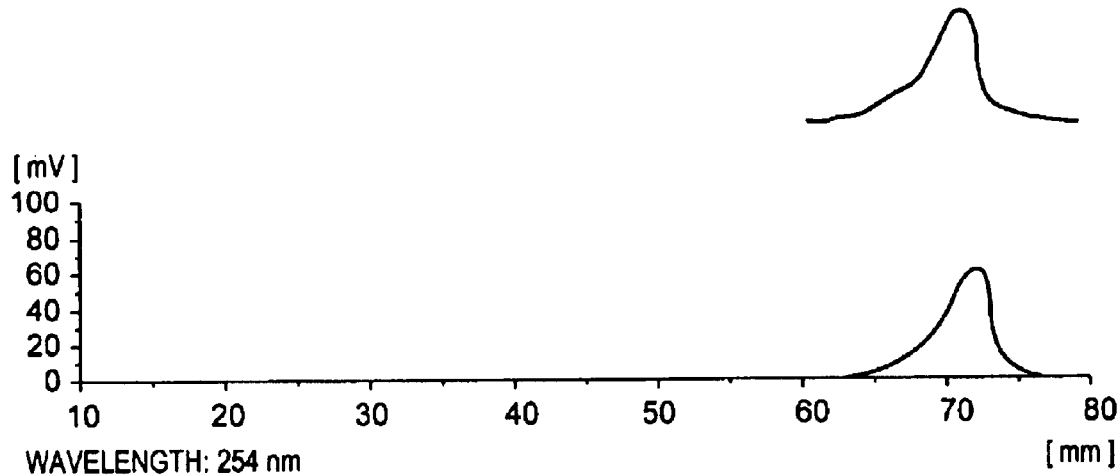
FIG. 2d

SUBMITTER: PUSHPA KHANNA

SAMPLE NAME: GOURDIN                                DATE:

|  |  |  |  |  |  |  |  | HIS |
|---|---|---|---|---|---|---|---|---|
| ASP | LEU |  |  |  | TYR |  | SER | ARG |
|  | VAL | SER | GLN | GLN | VAL | GLY — | GLN — | GLN |
| SEQUENCE: GLY — | ILE — | GLU — | GLU — | THR — | THR |  | THR | LEU |
| CYCLE #: 1 | 2 | 3 | 4 | 5 | 6 | 7 | 8 | 9 |

|  |  | ARG |  |  |  | GLY |  |  |
|---|---|---|---|---|---|---|---|---|
|  | TYR | HIS | HIS |  | ARG | ASP | ARG | ARG |
| LYS | ILE | ALA | GLU | ASN | MET | ASN | THR | HIS |
| SEQUENCE: ARG — | LEU — | LYS — | TYR — | ASP — | ILE — | LEU — | ASP — | ALA |
| CYCLE #: 10 | 11 | 12 | 13 | 14 | 15 | 16 | 17 | 18 |

| SER |  |  |  |  |  |  | PRO |  |
|---|---|---|---|---|---|---|---|---|
| GLU |  | SER |  | GLU |  | THR | ARG | HIS |
| LEU | ARG | PRO | ILE | LEU | PHE | SER | ALA | ARG |
| SEQUENCE: LYS — | GLU — | ALA — | ASP — | ILE — | TYR — | ASN — | HIS — | GLY |
| CYCLE #: 19 | 20 | 21 | 22 | 23 | 24 | 25 | 26 | 27 |

| GLY |  |  | VAL |  | PRO |  |  |
|---|---|---|---|---|---|---|---|
| VAL |  |  | LEU | ASN | ILE | ALA |  |
| SEQUENCE: ALA — | GLY — | ARG — | ILE — | SER — | THR — | VAL — | ASN |
| CYCLE #: 28 | 29 | 30 | 31 | 32 | 33 | 34 | 35 |

YIELD(pmol): ILE(2)    98.11      YIELD(pmol): GLU(3)    56.13

CARRYOVER: ILE(6)    22.6%       REP YIELD: ILE(2.23)   92.3%

SEQSTD YIELD: NL(6)    2.30  SEQSTD CARRYOVER: NL(6)    23.0%

SEQSTD REP YIELD:   NL(6.11)   97.0%

COMMENTS: Mixtures with interchangeable amino acid at positions 12,13,15-19, 25-27 and 31-34. Appears to be a mixture of sequences.

FIG. 3

Figure 1:
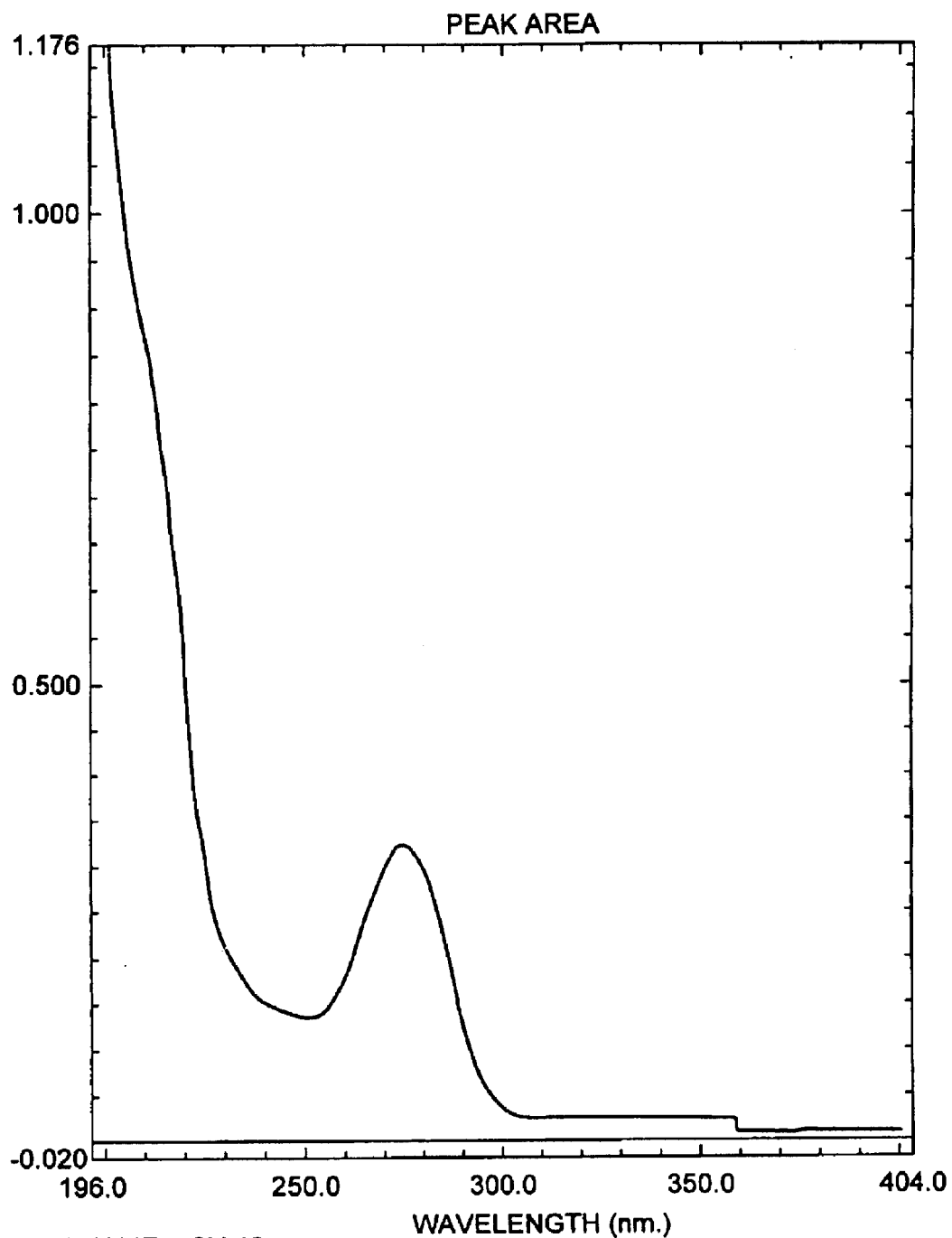
Figure 4C:
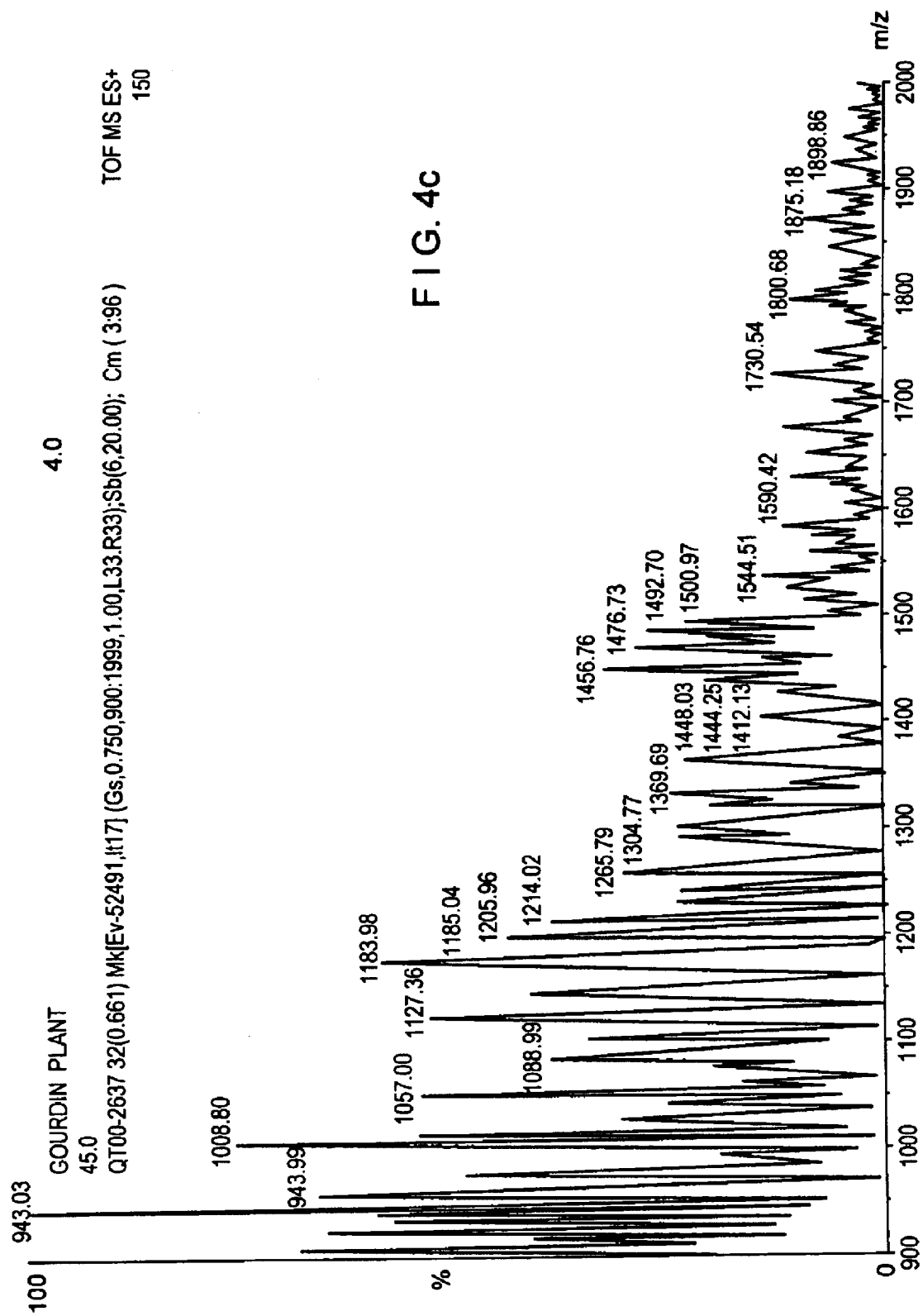

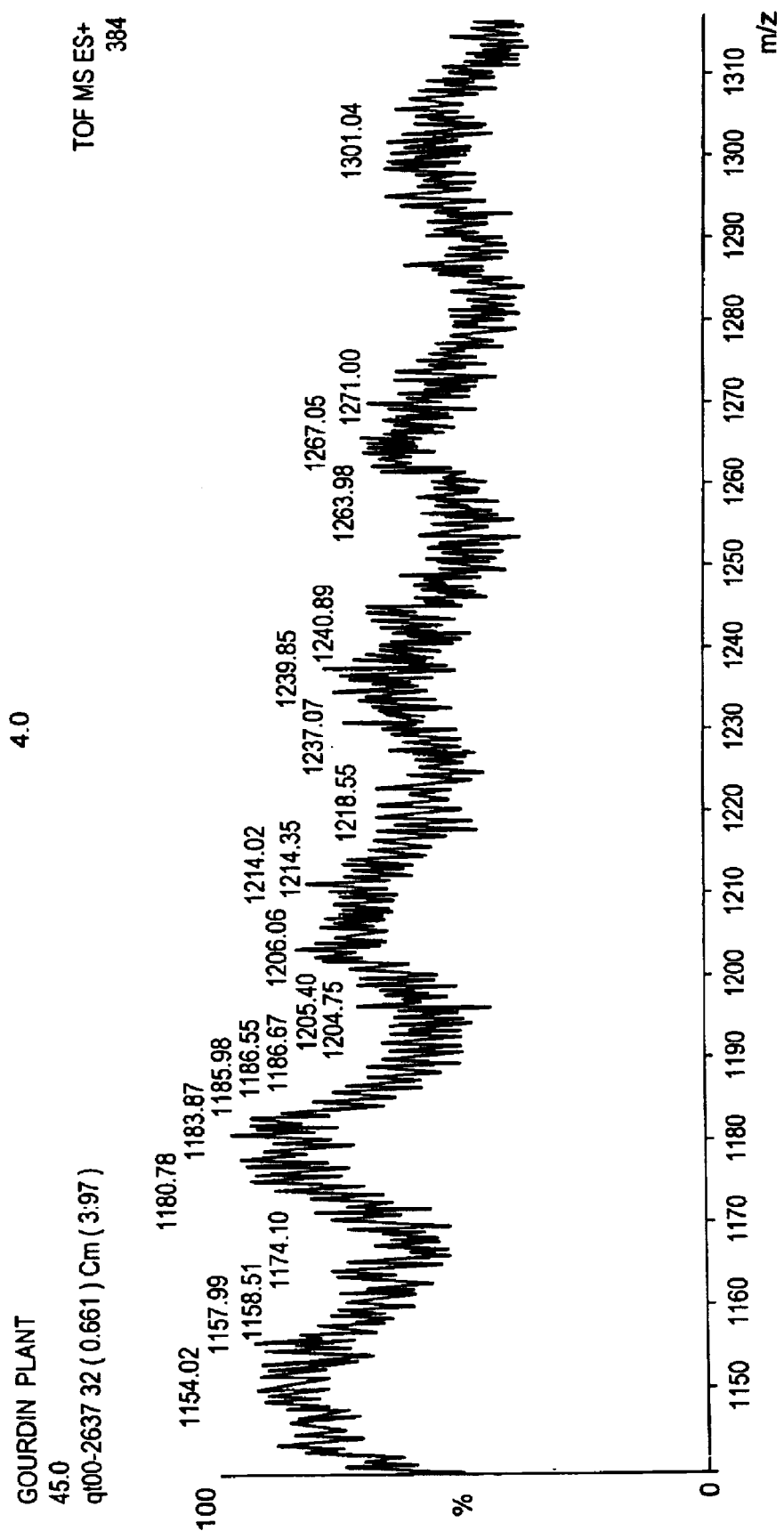
FIG. 4a1

Figure 2C:
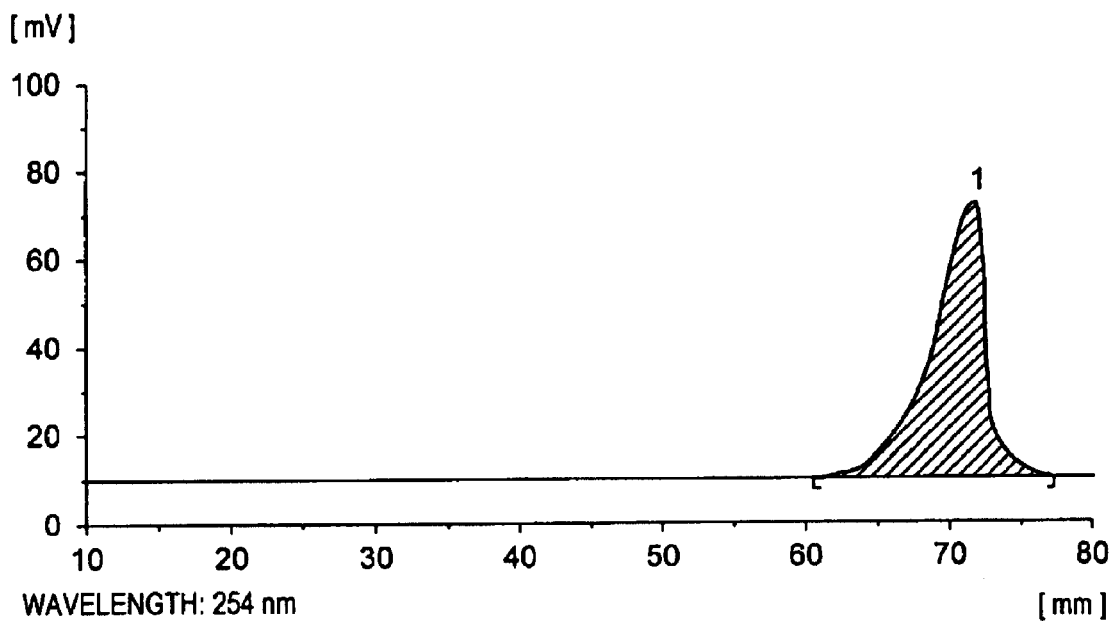

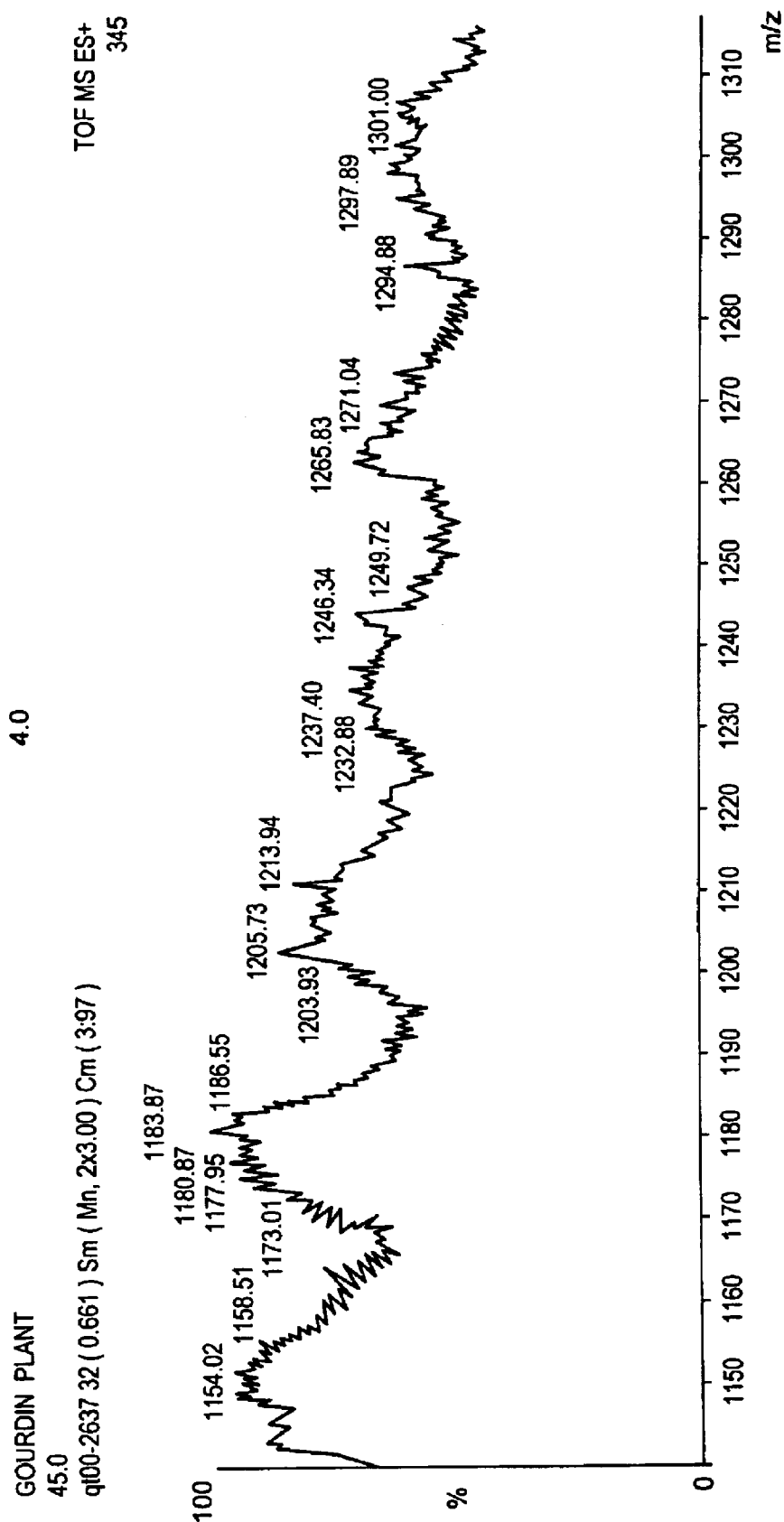
FIG. 4a2

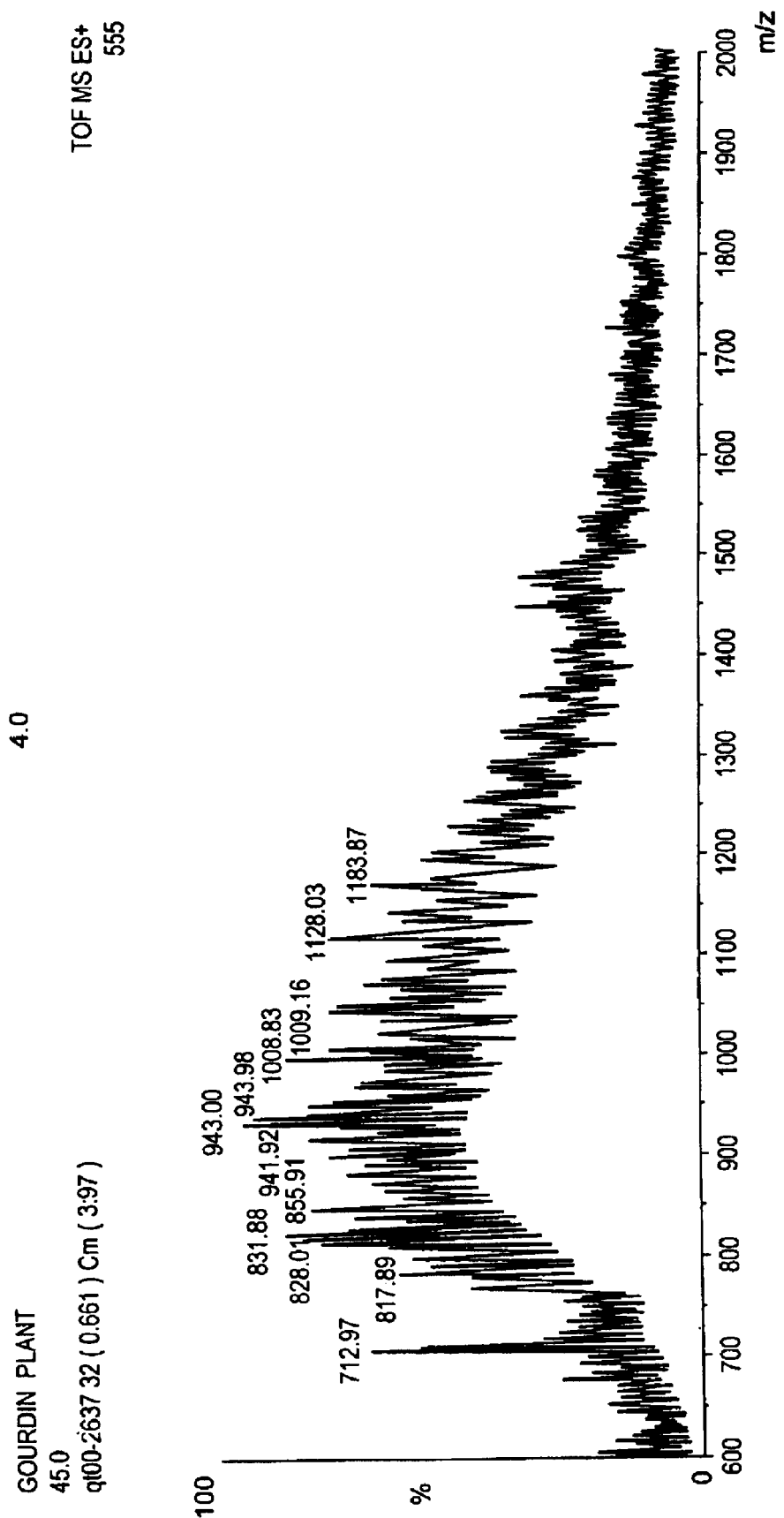
FIG. 4b1

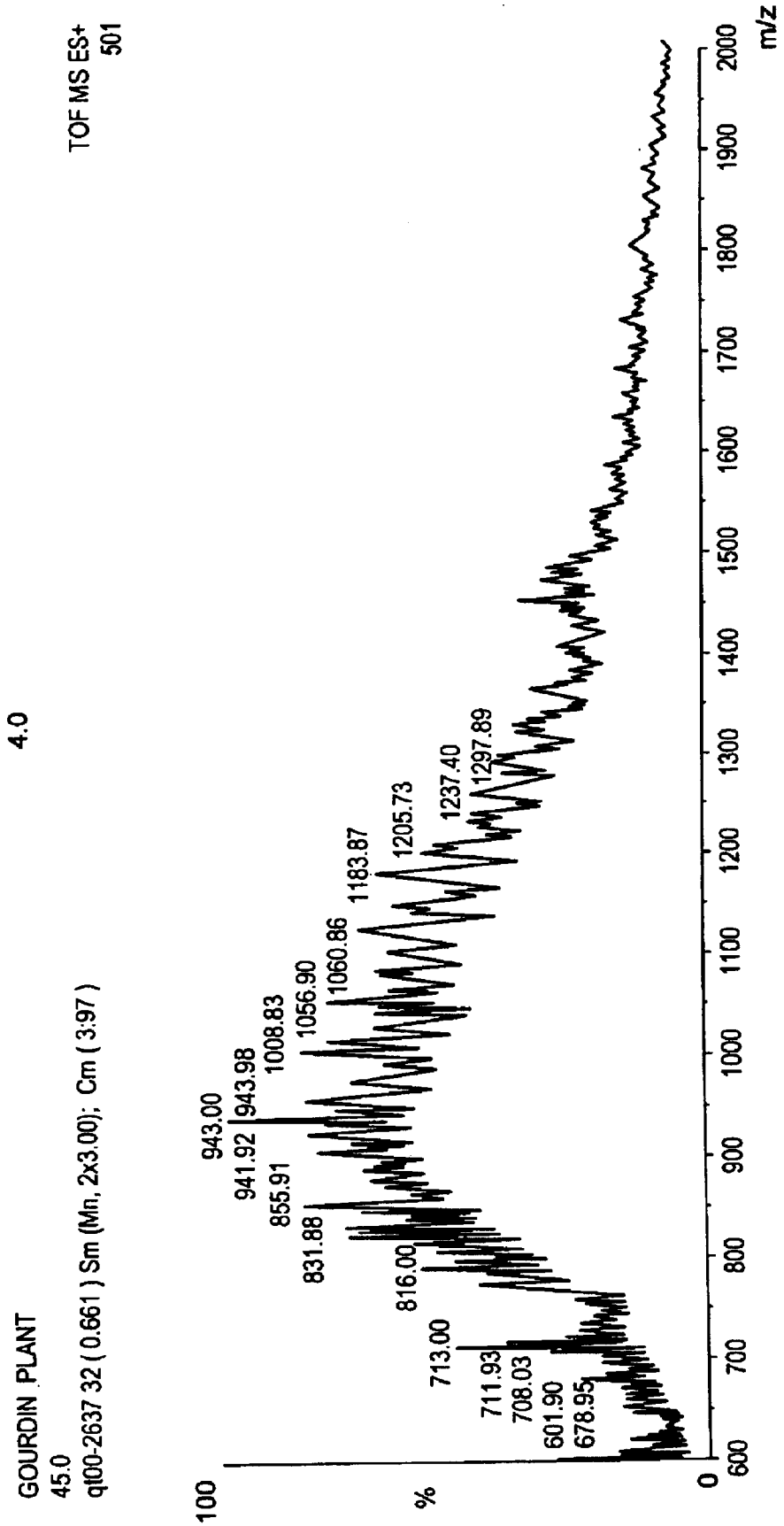
FIG. 4b2

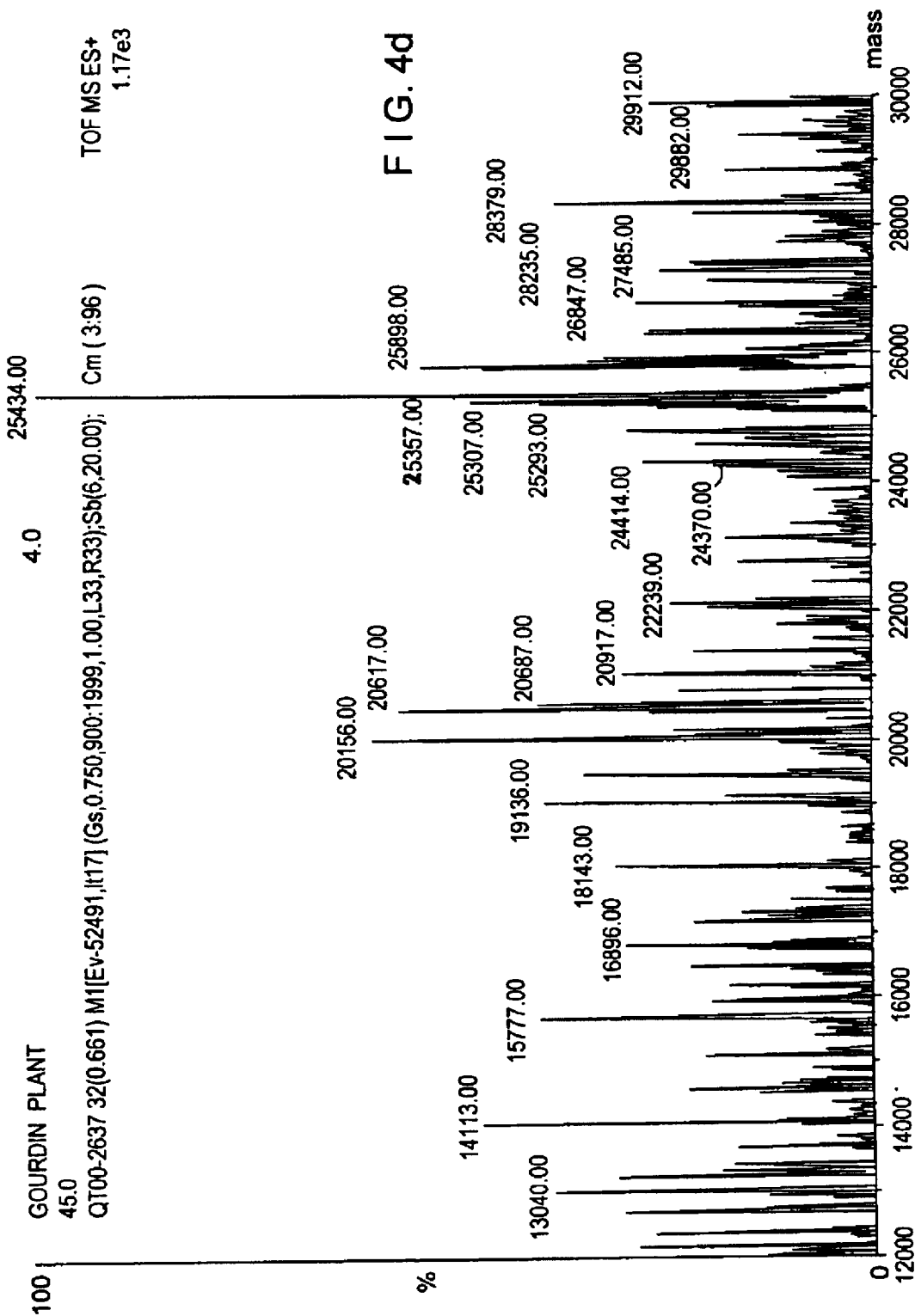

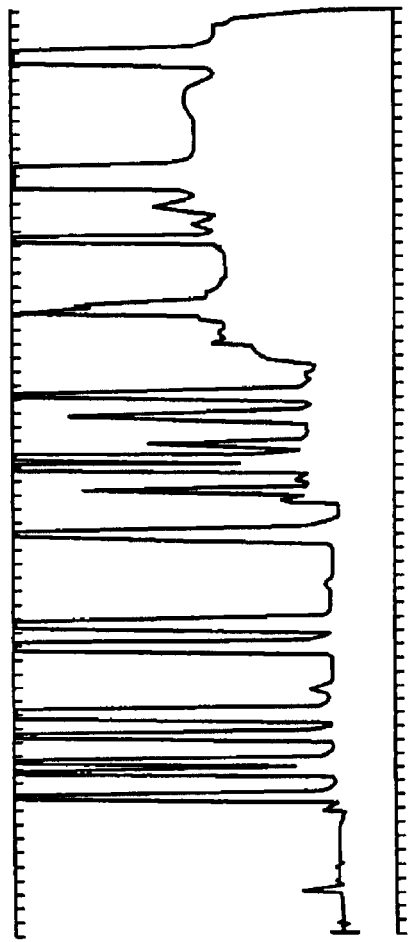

INTERFACE 01 0-68 Min   SCALE: 15 Mv Ch. A, 15 Mv Ch. B
AMINO ACID ANALYSI   PROCESSED: 11-22-2000 14:26:30, SEGMENT 17, CYCLE 936
RAW DATA SAVED IN FILE K: AAA936.PTS   SECOND CHANNEL STORED IN K: BAA936.PTS

EXTERNAL STANDARD TABLE

\*\*\*\*\*\*\*\*\*\*\*\*\*\*\*\* 11-22-2000   14 : 26 : 30    Version 4.1 \*\*\*\*\*\*\*\*\*\*\*\*\*\*\*\*

| | | | | Data File: K:AAA936 |
|---|---|---|---|---|
| Sample Name: amino acid analysis | | | | #457 |
| Date: 11-22-2000  14 : 26 : 30 | Method: F:REBECKA | | 11-22-2000   13 : 54 : 21 | |
| Interface: 0 | Cycle #: 936 | Operator  jmc | Channel #: 0 | Vial #: N.A. |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

Starting Peak Width: 21    Threshold: .5    Area Threshold: 500
Starting Delay:       0.00            Ending retention time:  68.00
Area reject:          5000            One sample per:         2.002 sec.
Amount injected:      1.00            Dilution factor:        1.00
Sample weight:        1.000000

SEE FIG. 5a2 →

F I G. 5a1

SEE FIG. 5a1

| PEAK NUM | RET TIME | PEAK NAME | CONCENTRATION in nmoles | NORMALIZED CONC | AREA | HEIGHT | AREA/HEIGHT | BL | REF PEAK | % DELTA RET TIME | CONC/AREA |
|---|---|---|---|---|---|---|---|---|---|---|---|
| 1 | 2.936 | | | 0.1504% | 20695 | 1550 | 13.4 | 1 | 6 | -1.592 | 3.4373E-06 |
| 2 | 8.609 | | | 0.0856% | 9566 | 696 | 13.7 | 1 | 6 | 0 | 4.28185E-06 |
| 3 | 9.543 | asx | 3.6346 | 7.6853% | 1019304 | 61489 | 16.6 | 1 | 6 | .5811 | 3.5658E-06 |
| 4 | 11.378 | thr | 1.1549 | 2.4420% | 314916 | 15245 | 20.7 | 2 | 6 | .1132 | 3.6674E-06 |
| 5 | 12.112 | ser | 2.0456 | 4.3254% | 595007 | 27668 | 21.5 | 2 | 6 | 0 | 3.4380E-06 |
| 6 | 14.081 | int. std. | 1.0397 | 2.1985% | 576309 | 23599 | 24.4 | 2 | 6 | 0 | 1.0041E-06 |
| 7 | 15.649 | glx | 6.6195 | 13.9567% | 1959672 | 71617 | 27.4 | 2 | 6 | .1667 | 3.3779E-06 |
| 8 | 17.651 | pro+ cys | 2.1133 | 6.1414% | 28161 | 809 | 34.8 | 2 | 6 | -.2854 | 1.0314E-04 |
| 9 | 20.554 | gly | 3.4509 | 7.2968% | 1098728 | 36599 | 30.0 | 2 | 9 | 0 | 3.1408E-06 |
| 10 | 22.256 | ala | 2.8168 | 5.9961% | 801412 | 25276 | 31.7 | 2 | 9 | 0 | 3.5248E-06 |
| 11 | 28.996 | val | 2.6160 | 5.4358% | 783543 | 16490 | 42.7 | 2 | 9 | 0 | 3.6541E-06 |
| 12 | 32.299 | ser | 0.5625 | 1.1894% | 157161 | 8772 | 17.9 | 1 | 9 | .0101 | 3.5792E-06 |
| 13 | 33.166 | | 0.0000 | 0.0000% | 10132 | 523 | 19.4 | 1 | 16 | 0 | 0.0000E+00 |
| 14 | 33.967 | ileu | 1.8404 | 3.8914% | 535119 | 23330 | 22.9 | 2 | 16 | -.0931 | 3.4392E-06 |
| 15 | 34.735 | leu | 3.1701 | 6.7031% | 953284 | 38035 | 25.1 | 2 | 16 | 0 | 3.3255E-06 |
| 16 | 35.902 | nl-std. | 6.2739 | 0.5791% | 163238 | 6196 | 26.3 | 2 | 16 | 0 | 1.6777E-06 |
| 17 | 37.871 | tyr | 1.0645 | 2.2508% | 290327 | 9412 | 30.8 | 1 | 16 | 0 | 3.6666E-06 |
| 18 | 39.473 | phe | 1.6115 | 3.4075% | 408260 | 12881 | 31.7 | 2 | 16 | 0 | 3.9472E-06 |
| 19 | 45.479 | his | 1.2110 | 2.6711% | 203562 | 8185 | 24.9 | 1 | 16 | 0 | |
| 20 | 46.013 | | 0.0000 | 0.0000% | 154147 | 5442 | 26.3 | 2 | | | 0.0000E+00 |
| 21 | 50.751 | lys | 1.2451 | 2.6327% | 385456 | 13267 | 29.1 | 2 | 16 | 0 | 3.2302E-06 |
| 22 | 51.885 | | | 0.3929% | 32441 | 913 | 35.5 | 2 | 16 | 0 | 5.7275E-06 |
| 23 | 53.287 | | 0.0000 | 0.0000% | 102408 | 2246 | 46.6 | 2 | | | 0.0000E+00 |
| 24 | 55.355 | NH4 | 6.1666 | 13.0391% | 3568874 | 61870 | 57.7 | 2 | 16 | 0 | 1.7279E-06 |
| 25 | 64.197 | arg | 3.5602 | 7.5279% | 1016938 | 22156 | 45.9 | 1 | 16 | 0 | 3.5009E-06 |

TOTAL AMOUNT: 47.2934

FIG. 5a2

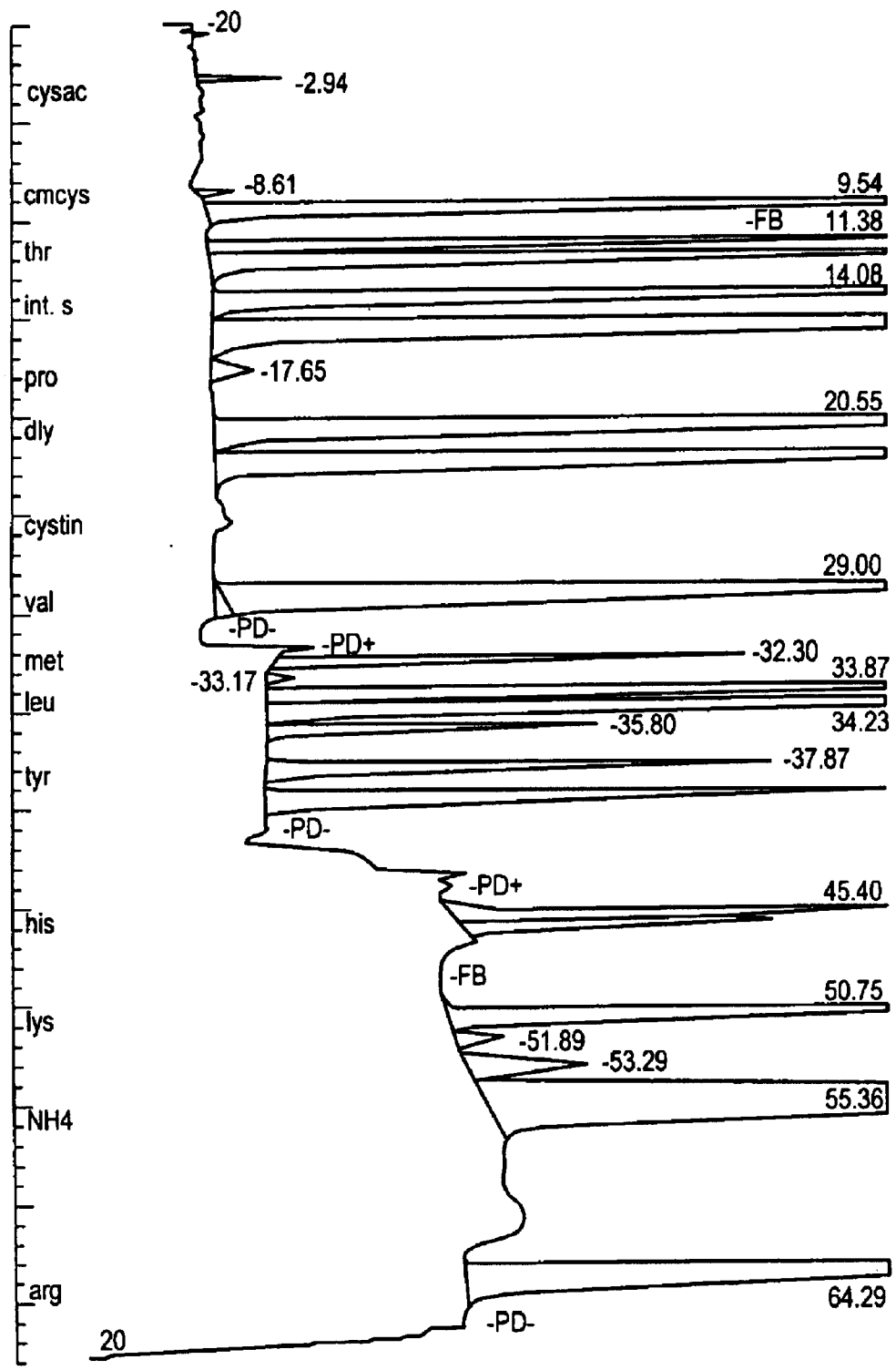
F I G. 5b

EXTERNAL STANDARD TABLE

```
************* 11-22-2000  14:28:43   Version 4.1 *************
Sample Name: amino acid analysis                              Data File: K:BAA936
Date: 11-22-2000   14:26:30   Method: F:REBECKA      11-22-2000   13:55:21   #257
Interface: 0       Cycle #: 936      Operator jmc         Channel #: 1       Vial #: N.A.
Starting Peak Width: 21    Threshold: .5    Area Threshold: 500

Starting Delay:      0.00                            Ending retention time:    68.00
Area reject:         5000                            One sample per:          2.002 sec.
Amount injected:     1.00                            Dilution factor:          1.00
Sample weight:       1.000000
```

| PEAK NUM | RET TIME | PEAK NAME | CONCENTRATION in nmoles | NORMALIZED CONC | AREA | HEIGHT | AREA/ HEIGHT | BL | REF PEAK | % DELTA RET TIME | CONC/ AREA |
|---|---|---|---|---|---|---|---|---|---|---|---|
| 1 | 8.775 |  | 0.0000 | 0.0000% | 5143 | 286 | 18.0 | 1 |  |  | 0.0000E+00 |
| 2 | 9.510 |  | 0.0000 | 0.0000% | 129394 | 7707 | 16.8 | 1 |  |  | 0.0000E+00 |
| 3 | 11.345 |  | 0.0000 | 0.0000% | 24969 | 1171 | 21.3 | 2 |  |  | 0.0000E+00 |
| 4 | 12.079 |  | 0.0000 | 0.0000% | 59106 | 2389 | 24.7 | 2 |  |  | 0.0000E+00 |
| 5 | 14.047 |  | 0.0000 | 0.0000% | 47121 | 1978 | 23.8 | 1 |  | .2393 | 0.0000E+00 |
| 6 | 15.616 | glx | 6.2317 | 74.6757% | 375516 | 13802 | 27.2 | 1 | 7 | 0 | 1.6595E-05 |
| 7 | 17.651 | pro+cys | (2.1133) | 25.3244% | 199944 | 6665 | 30.0 | 1 | 7 |  | 1.0570E-05 |
| 8 | 20.554 |  | 0.0000 | 0.0000% | 83682 | 2753 | 30.4 | 1 |  |  | 0.0000E+00 |
| 9 | 22.222 |  | 0.0000 | 0.0000% | 67237 | 2027 | 33.2 | 1 |  |  | 0.0000E+00 |

TOTAL AMOUNT: 8.3451

SEE FIG. 5c2

FIG. 5c1

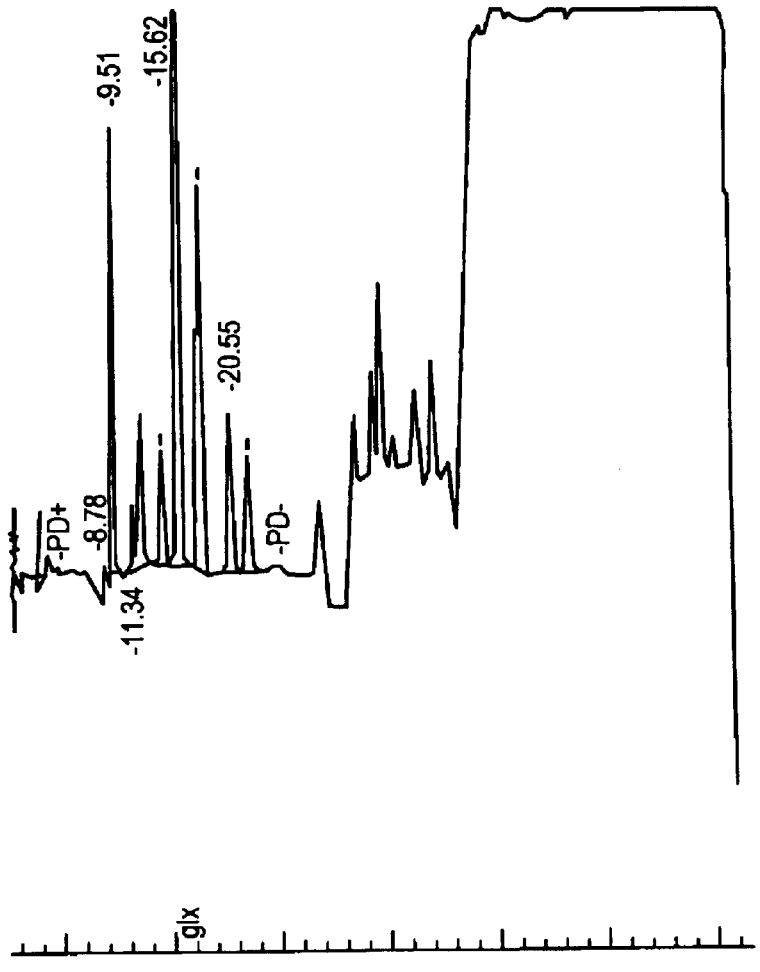
FIG. 5c2

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence:
      Polypeptide-p isolated from momordica charantia

<400> SEQUENCE: 1

Asp Thr Ser Glu Pro Gly Ala Val Cys Met Ile Leu Tyr Phe His Lys
 1               5                  10                  15

<210> SEQ ID NO 2
<211> LENGTH: 18
<212> TYPE: PRT
<213> ORGANISM: Artificial Sequence
<220> FEATURE:
```

-continued

```
<223> OTHER INFORMATION: Description of Artificial Sequence:
      Polypeptide-k isolated from momordica charantia

<400> SEQUENCE: 2

Asx Thr Ser Glx Pro Cys Gly Ala Val Met Ile Leu Tyr Phe His Lys
 1               5                  10                  15

Trp Arg
```

PROTEIN/POLYPEPTIDE-K OBTAINED FROM *MOMORDICA CHARANTIA* AND A PROCESS FOR THE EXTRACTION THEREOF

This application is a continuation-in-part of International Application PCT/IN99/00052 filed on Sep. 28, 1999, claims the benefit thereof and incorporates the same by reference.

FIELD

This invention relates to a highly effective hypoglycaemic protein called polypeptide-k, extracted from *Momordica charantia*. This invention also provides a method for the extraction of said polypeptide-k from *Momordica charantia*. Further, the invention provides a novel hypoglycaemic composition employing the said protein, and useful in the treatment of diabetes mellitus.

BACKGROUND

Insulin has hitherto been commercially synthesized from the pancreas of animals and human insulin from *E. coli* (Eli Lily, U.S.A.). So far there is no report of commercial extraction of insulin like polypeptide from plant source.

Isolation of insulin from animal pancreas is open to objection due to the following reasons:

1. By killing 10,000 animals only one pound of pure insulin is obtained.

2. It is not being sublingually administered.

3. If the pancreas is infected by some diseases there is always a probability of its being carried (if it is a virus) along with the insulin.

4. Human insulin can be synthesised from *E. coli* which is expensive.

Hence, to obviate these and other drawbacks in conventional insulin extraction methods, scientists focussed on plant based products.

*Momordica charantia* is a perennial herb of the family Cucurbitaceae, widely grown in Asia. The herb is endemic to tropical regions like India, S. Africa, Philippines, China and Burma. The species of Momordica found in western countries are different from the tropical species in that, the plants differ in morphological and organoleptic properties.

Various parts of this plant, especially the fruits, have been widely used for preparation of hypoglycaemic pharmacological compositions.

In Indian Patent No. 136565, the applicant has disclosed a method for the extraction of a protein called 'polypeptide-p' from *Momordica charantia*. The dried and pulverized fruits and tissue cultures of Momordica are separately extracted in ethanol and then mixed with cold ethanol and diethyl ether. Thereafter, needle-like crystals are formed by adding zinc in traces after 18 hr. The fruits and cultures are separately crushed, homogenized in water, ethanol and concentrated sulfuric acid is added for adjusting pH to 3, thereby obtaining flocculent precipitates.

This method had the following drawbacks:

1. The use of alcohol in the extraction procedure was not practical due to its unavailability in large amount and the impurities present in it.

2. The use of raw material as fruits and tissue culture creates problems in handling, uneconomically viable and the yield was very poor.

The drawbacks of this patent were obviated in another Indian Patent No. 176040. This patent discloses a process for extraction of a highly effective polypeptide-p by using hexane along with diethylether. Although the process developed and disclosed in above referred patent resulted in good yield, improved purity and high efficacy of the drug by removal of oil and sapogenins and other contaminants therefrom, yet, it had a few drawbacks, some of which a few are given below:

1. The purification of polypeptide-p was a cumbersome method due to the presence of interfering radicals as oil and sapogenins.

2. Use of diethylether in the extraction procedure was not practical due to its highly inflammatory nature and high cost.

3. The presence of pesticides/insecticides/urea and other contaminants affected the purity of polypeptide-p.

4. The yield was not optimum.

This protein called 'polypeptide-p' (SEQ ID NO: 1) was extracted from the fruits and tissues of *Momoridca charantia*. This protein comprised amino acids as shown in Table 1 below:

TABLE 1

| Amino acid | $\mu$ Moles/mgs | Molecular number |
| --- | --- | --- |
| Aspartic acid | 0.273 | 17 |
| Threonine | 0.138 | 8.7 |
| Serine | 0.195 | 12 |
| Glutamic acid | 0.305 | 19 |
| Proline | 0.159 | 10 |
| Glycine | 0.225 | 19 |
| Alanine | 0.240 | 15 |
| Valine | 0.174 | 11 |
| ½ Cysteine | 0.058 | 3.6 |
| Methionine | 0.031 | 2 |
| Isoleucine | 0.116 | 7 |
| Leucine | 0.207 | 13 |
| Tyrosine | 0.016 | 1 |
| Phenylalanine | 0.082 | 5 |
| Histidine | 0.066 | 4 |
| Lysine | 0.209 | 13 |
| Arginine | 0.161 | 10 |
| $NH_3$ | 0.431 | (27) omit 166 |
| TOTAL | | residues |
| Approximate molecular weight 11,000 | | |

U.S. Pat. No. 5484889 describes a plant protein useful for treatment of tumors and HIV infection. The protein has been obtained from the seeds of *Momordica charantia*. It is pertinent to note that this protein isolated and purified is a ribosome inactivating protein and hence, useful in tumor therapy. The processes described for the extraction of the protein involve use of solvents and the tedious process of chromatography, dialysis etc. In the processes described in this patent as well as in Indian patent No. 176040, the yield, purity were low and had several contaminants. Accordingly, to obviate these and other drawbacks, the applicant has isolated a novel protein called 'poplypeptide-k' having hypoglycaemic property from *Momordica charantia* and has also devised a novel process for extraction of the protein from the same source. The letter 'k' is derived from the term 'karela' which means 'bitter gourd' or *Momordica charantia* in a main Indian language.

OBJECTS OF THE INVENTION

The main object of the invention to provide a novel protein called 'polypeptide-k'.

It is an object of the invention to provide a process for the extraction of a protein called 'polypeptide-k' from the dry seeds of *Momordica charantia*.

Another object is to prepare a novel hypoglycaemic composition using the said protein.

Yet another object of the invention is to provide a hypoglycaemic composition containing 'polypeptide-k' for treatment of diabetes in human beings and animals.

Still another object of the invention is to provide a novel protein called polypeptide-k which is capable of reducing high blood pressure and increasing immunity in human beings and animals.

One more object of the invention is to provide a novel protein namely polypeptide-k which takes care of neuropathy and makes the patient feel normal.

SUMMARY OF THE INVENTION

In accordance with the above and other objectives, the invention provides a novel protein 'polypeptide-k' extracted from *Momordica charantia*, a process for the extraction of the said polypeptide-k and a novel hypoglycaemic composition employing the novel polypeptide of the invention.

DETAILED DESCRIPTION OF THE INVENTION

Accordingly, the invention provides a method for the extraction of proteins from dry seeds of *Momordica charantia*, said process comprising the steps of:

i) grinding the dry seeds to a fine powder in a suitable mill, ii) treating the pulverized seeds with a mixture of hexane-acetone, iii) dissolving the residual mass in about 80% aqueous acetone, iv) adjusting the pH upto 9.5 by adding suitable organic buffer like ammonium hydroxide, v) treating the supernatant layer with sulfuric acid, vi) collecting the flocculent precipitate of polypeptide-k and isolating the protein by selective crystallisation.

Thereafter, the protein is analysed by chromatography.

The protein isolated in the present invention i.e. 'polypeptide k' is different as compared to the protein in the prior art. To describe in detail, the protein isolated in the present invention is a protein having 18 amino acids, and is called 'polypeptide k'. The process for extraction of the protein consists of de-oiling of the washed seeds of *Momordica charantia*, using hexane and a little acetone in the ratio of 3:1. The dry seeds are used because polypeptide-k is a storage protein and it gets accumulated in large quantities when the seed is dried. After de-oiling, the seeds are dried, powdered and dissolved in water and acetone taken in the ratio of 3:1. A mixture is made and then the pH is adjusted to 9.5 by adding ammonium hydroxide. Supernatant was remove and the pH was adjusted to 3 by adding sulfuric acid. The flocculent precipitate was collected and dried. The dried mass was powdered and washed with water and acetone to remove oil, salts and other undesirable material, till it gives a single spot in TLC and HPLC.

In one embodiment, the dried seeds of *Momordica charantia* are split, washed thoroughly with water 2–3 times to render it substantially free from impurities and dried under vacuum, before extraction of the protein.

In another embodiment, the solvents used for removal of the oils from the seeds comprise a mixture of hexane and acetone in the ratio of 3:1.

In one embodiment, thin glass plated (20×20) coated (0.4 mm to 0.5 mm thick) with silica gel G are activated at 100° C. The solution of insulin is applied, the plates developed in n-butanol, acetic acid water (12:5:2) are dried, and single spot nearly corresponding to standard insulin visualized by spraying nin-hydrin (0.25%) in acetone, isolated along with silica gel G from unsprayed plates, extracted in 50% ethanol buffered with ammonium hydroxide or 10% of formic acid, filtered, the filtrate dried and pure white needle-like crystals formed.

In yet another embodiment, when the analysis is carried out, the isolated substance is hydrolyzed along with the standard insulin, applied on paper chromatograms separately, developed, yielding 18 amino acids including glutamine. This isolated substance is a protein named as 'polypeptide-k'.

In another feature, the isolated substance and the standard insulin are hydrolyzed separately by 6 N HCl for 20 hours, dried, reconstituted in 50% ethanol, applied on Whatman No. 1 filter paper strips developed in n-butanol, acetic acid, water (60:20:20), strips developed sprayed with 0.25% nin-hydrin in acetone. The standard hydrolyzate shows presence of 18 amino acids including glutamine.

In the analysis is carried out, the seeds are extracted in hexane acetone yielding a product which has a melting point (234° C.), Gel electrophoretic pattern of the accompanying drawings and number of amino acids of the standard insulin except glutamine being extra in polypeptide-k.

It may be noted that most of the plant parts of Momordica contain the protein disclosed by the invention, in varying degrees. As such, the protein polypeptide-k may be extracted from the dry seeds.

The dried seeds are processed using hexane (food grade) along with acetone instead of ether as used in the process described in earlier Patent No. 176040. The process has resulted in high yield, improved purity and high efficacy of polypeptide-k by removal of undesired oils, flavonoids and sapogenins therefrom.

The Applicant has analyzed the peptide isolated from *Momordica charantia* and found that this protein has 18 amino acids. The $18^{th}$ amino acid is glutamine. The UV spectrum has shown absorption peak at 275 nm whereas the peak for polypeptide-p, i.e. another protein found in *Momordica charantia* is noticed at 250 nm. BPLC analyses for the protein polypeptide-k shows a single peak. Thus, the mass spectrum analyses done for polypeptide-k discloses the fact that polypeptide-k consists of two peptide chains as opposed to a single chain present in polypeptide-p.

Another notable feature is that polypeptide-p can be isolated from the fruits, fresh seeds and tissues of *Momordica charantia*. Whereas, polypeptide-k is obtained from the dried seeds of *Momordica charantia* as a storage protein.

More importantly, the earlier isolated polypeptide-p has approximate molecular weight of 11,000 kd whereas polypeptide-k of the present invention has an approximate molecular weight of 18,000 kd.

Thus, polypeptide-k (SEQ ID NO:2) differs from polypeptide-p in the following respects:

1. The polypeptide-k has 18 amino acids whereas polypeptide-p has only 17 amino acids. The extra amino acid present in polypeptide-k is glutamine.

2. The approximate molecular weight of polypeptide-k is 18,000 units whereas the weight of polypeptide-p is 11,000.

3. Polypeptide-k has a free N-terminal.

4. Polypeptide-k is not water soluble whereas polypeptide-p is partially water soluble.

5. Polypeptide-k is not injectible to a patient and can be administered orally only through sub-lingual route whereas polypeptide-p is injectible as described. In other words, polypeptide-p is injectible (intramuscular) and this is inconvenient to patients, however, polypeptide-k is taken sublingually from the above surface of the tongue and its administration and absorption is easy, acceptable and convenient to patients.

6. Polypeptide-k is stable and the life is about 18 months (kept at normal pressure and temperature). On the other hand, polypeptide-p is unstable and its life is hardly 2–3 months when kept at normal pressure and temperature.

7. Polypeptide-k has the combustion point (m.p) of 234° C., whereas polypeptide-p has early combustion point which starts at 228–232° C.

Diabetes is a disease wherein glucose is not utilized as an energy source in the body such glucose remains at a high levels in the blood and eventually gets excreted through urine. In some conditions, insulin secreted from beta cells of pancreas is insufficient or does not sufficiently fulfill its function.

Diabetes is generally classified into insulin-dependent diabetes (Type I diabetes) and non-insulin-dependent diabetics (Type II diabetes). Type I diabetes is in the state of lowering of the function of pancreatic beta cells resulting from hereditary cause, viral infection obesity, drug effect, accident, etc. wherein insulin is not efficiently secreted, and suddenly attacks mainly in the twenties to thirties. Although it is not sure, onset of type II diabetes in the forties or in cases with family history of diabetes, obesity, stress, etc. In the case of type II diabetes, since insulin is sufficiently secreted from pancreas but insulin resistance and glucose utilization are different from those of normal person, blood sugar is not returned to normal level in spite of hyperinsulinemia.

Diabetes is accompanied with numerous symptoms. Typical examples of such symptoms are polyuria, excessive drinking and polyphagia. That is, diabetic patients exhibit polyuria which is caused by excretion of glucose and excessive water through urine by the action of osmotic pressure originated from high blood glucose level, and therefore, complain of thirst caused by dehydration, which induces excessive drinking, and causes the empty of stomach to intake excess of food. Diabetic patients cannot efficiently utilize glucose as an energy source and, instead, utilize protein and fat as preserved in the body, and this phenomenon is caught in a vicious cycle causing reduction in body weight.

However, such phenomena are merely acute symptoms observed in the primary stage of diabetes. If diabetes becomes chronic by delay of treatment, chronic vascular diseases add up as complications. Thus, diabetic complications such as diabetic retinopathy (visual disturbance, blindness, retinal hemorrhage), diabetic nephropathy, diabetic peripheral neuropathy, etc. reduce general metabolic and sensory function of human body.

A number of medicines have been produced and tested act to lower blood sugar of a non-insulin dependent diabetics. However, majority of these medicines have one or more undesirable features, some of them have significant side effects for a large portion of the population, or a large dosage is necessary. Also, some of them reduce the blood sugar level too much so that they can only be used sporadically or they can be a threat to health, and others have possible toxicity. At present, there is no natural antidiabetic drug which is highly effective at lowering blood sugar, yet does not lower it to an unsafe level, and has no significant side effects.

According to the present invention, a pharmacologically active hypoglycaemic agent is produced in a simple and straightforward way using only the protein of the invention.

Since it is very effective, relatively small amounts of the homeopathic medicine need be ingested in order to reduce the blood sugar level.

Herbal Compositions Using the Protein of the Invention

The protein extracted from *Momordica charantia* exhibits hypoglyceamic properties and accordingly compositions comprising the protein can be used for the treatment of hypoglycemia in mammals. The protein obtained from Momordica is in the form of an amorphous powder. The protein activates the inactive insulin and, thus, it can rejuvenate the pancreas depending upon the chronicity of the pathological condition of the individual. In fact, in course of time, it may act as a cure for diabetes. The applicant has conducted more than 500 experiments and confirmed that the single dose to about 12 mg to 70 mg of the protein at a time is quite effective. Accordingly, it is advisable that compositions containing the protein in single dose should comprise about 12 mg or more of the protein.

Hypoglyceamic compositions using the proteins of the invention can be formulated in a variety of physical forms such as tablets, edible products. For preparation of a tablet, about 12 mg to 70 mg of the protein is mixed with pharmacologically acceptable carriers suitable for consumption. The pharmacologically acceptable carrier must be of sufficient purity non-toxicity and should not interfere with the activity/efficacy of polypeptide-k. Edible products like biscuits, chewing gums, losenzes etc., which are not instantly swallowed can be prepared. In all such preparations, the content of the protein is about 12 mg to 70 mg. It is found that low salt biscuits prepared using the protein of the invention are very popular with diabetics.

It is pertinent to note that the hypoglyceamic composition of the invention is to be consumed 10 minutes before meals, at least 4 times a day. The most important aspect is that the tablet or the hypoglyceamic composition should only be chewed and should not be swallowed instantaneously.

In a feature of the invention, the hypoglyceamic composition herein described has no side effects. It can be consumed without restricting the use of other therapies. It has no cross reaction with insulin.

The invention is described in detail with reference to the following drawings wherein:

FIG. 1 represents the results of UV analysis of polypeptide-k.

FIGS. 2 (*a*) to (*d*) represents the results of high performance liquid chromatography depicting a single main peak, FIG. 3 represents the amino acids of polypeptide-k.

Figure 4E:
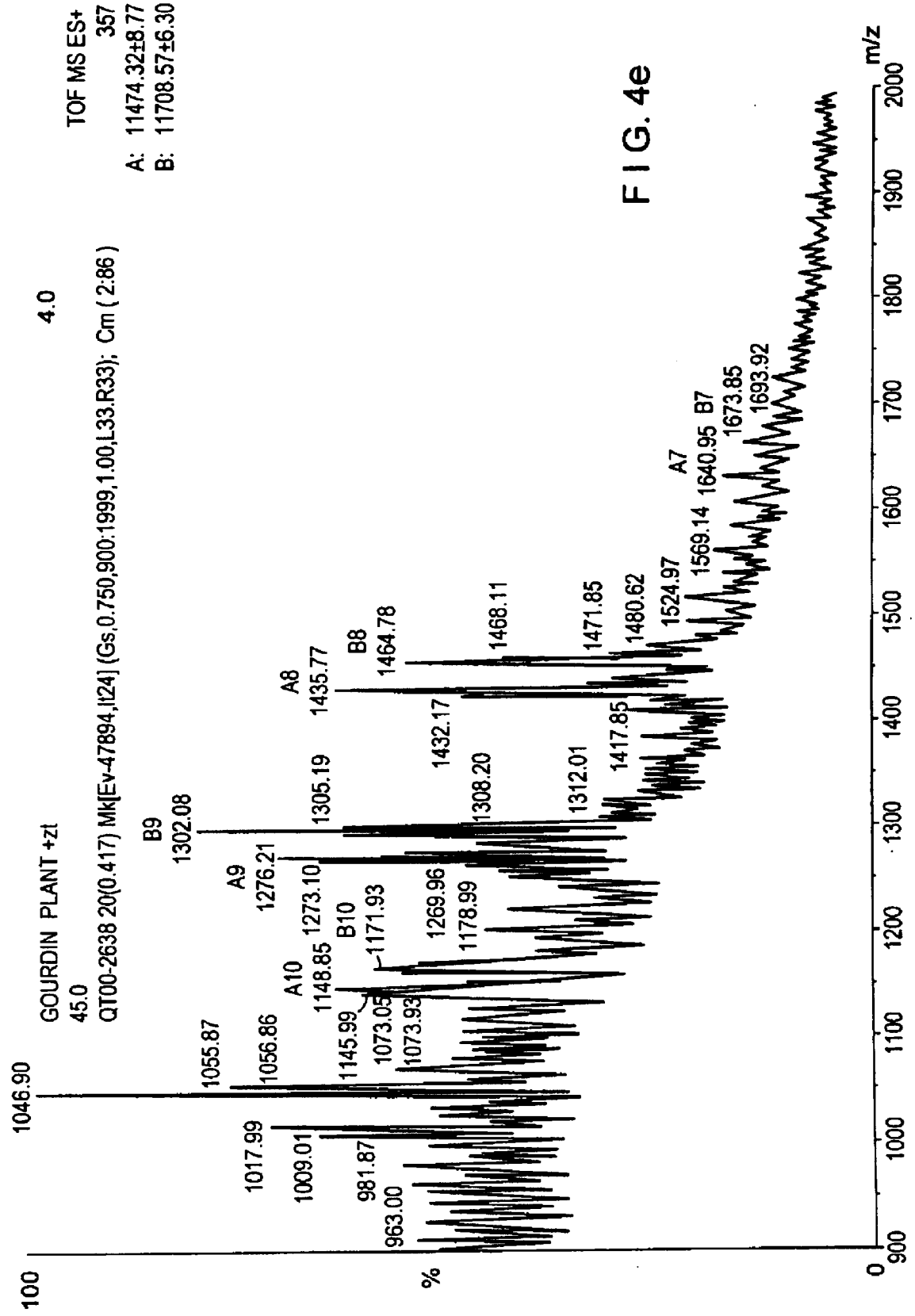

FIGS. 4 (*a*) to (*e*) represents the results of mass spectrum analysis done in respect of polypeptide-k. it clearly shows that polypeptide-k consists of two peptide chains.

FIGS. 5 (*a*) to (*c*) represents the results of IPLC analysis done in respect of polypeptide-k.

The invention is also illustrated by the following examples. Several modifications that may be apparent to those in the art are deemed to be included within the scope of the invention.

EXAMPLE 1

Protein Preparative Example

Extraction of protein from *Momordica charantia* L: 100 gms of dry seeds were taken from the ripe fruits of *Momordica charantia* L. The seeds were split manually. The split seeds were then thoroughly washed with water 3–4 times to render them substantially free of all impurities. The split seeds were then dried under vacuum and pulverized to a fine powder using a milling device. Any other conventional device may also be used.

The fine powder was then treated with acetone hexane solvent mixed in the ratio 1:2 for de-oiling the powder and the residual mass was dissolved in 20% acetone. The pH was adjusted to 9.5 by adding ammonium hydroxide, the supernatant thus obtained was buffered with $H_2SO_4$ to adjust pH3 for obtaining flocculent precipitate which were collected and crystallised with zinc acetate used in traces.

Thin glass plated (20×20 cm) coated (0.4 mm to 0.5 mm thick) with silica gel G (Kieselgel G nach Stahl; E. Merck) were activated at 100° C. for half an hour. The solution containing the isolated substance was applied 1 cm above the edge of the plates were run in an organic solvent mixture of n-butanol and acetic acid and water. It should be n-butanol acetic acid and water (12:5:2). The developed plates were dried at room temperature and sprayed with 0.25% nin-hydrin in acetone. The nin-hydrin positive spots (R=0.19) of the isolate nearly corresponding to insulin were collected from about 200 unsprayed plates along with the silica gel G and extracted with 50% ethanol buffered with ammonium hydroxide/10% formic acid. The extract was filtered and dried in vacuo. Pure colorless crystals thus obtained were weighed (3 g/100 gram dry weight of seeds).

The melting point of the purified compound (232°–235° C.) as well as the mmp (234° C. were determined. The melting point of the standard insulin was recorded as 233° C.

The standard sample of insulin as well as the isolated were hydrolyzed under reflux with 6N HCI for 20 hours separately. The hydrolyzates were filtered, dried, reconstituted separately in 50% ethanol or 10% formic acid and applied on strips of Whatman No. 1 paper. The paper strips were run in an organic solvent mixture of n-butanol, acetic acid and water (3:1:1). The hydrolyzates of both the isolated and the standard insulin were also applied separately along with the known amino acids (including hydroxylysine, methionine, hydroxyproline and trytophan). The various developed chromatograms were sprayed with 0.25% nin-hydrin in acetone. The amino acids of the hydrolyzate of the standard coincided exactly with those of the hydrolyzate of the isolated compound except glutamine being an extra amino acid in isolated polypeptide-k. Hydroxylysine, hydroxy-proline and tryptophan were found to be absent from the hydrolyzate of the isolated polypeptide-k as well as of the standard hydrolyzate which gave an indication that the isolated protein is marked by the presence of glutamine. Some of the amino acids identified in polypeptide-k are shown in FIG. 1.

Disc electrophoresis was carried out (10% SDS Biophore Gel, run in Tris buffer, operating pH 6.1, 3% acetic acid in lower cell; 90 V, mA 2.5 per tube; Bromophenol blue tracking dye). Samples of the crystallized isolate and bovine containing dithiothreltol and EDTA, injected and run for 7 hr. Gel collected from the tubes were stained (0.05% coomassie Brilliant Blue R-250 in 7% aqueous acetic acid) and washed with 10% acetic acid. Electrophoretic pattern of both the isolate and the bovine insulin were nearly identical as shown in FIG. 1 of the accompanying drawings. Immunoassays of polypeptide-k did not show any cross reaction when tested with bovine insulin.

Sublingual administration of the isolate showed positive and highly effective hypoglycaemic activity. When five hundred diabetic patients were treated (Table 3) no side effects of the drug were observed. Neuropathy, lethargieity, hypoglycaemia were not reported in these patients even when the drug was administered for a period of 2–4 years. At the same time, sugar level in the blood come down appreciably in one month time. The results are shown in table 3.

EXAMPLE 2

Extraction of Protein from *Momordica charantia* L.

200 gms of dry seeds were taken from the ripe fruits of *Momordica charantia* L. The seeds were spilt manually. The split seeds were then thoroughly washed with water 3–4 times to render them substantially free of all impurities. These seeds were then dried under vacuum and pulverized to a fine powder using a milling device. Any other conventional devices may also be used.

The fine powder was then treated with acetone hexane solvent mixed in the ratio 1:2. Thin glass plated (20×20 cm) coated (0.4 mm to 0.5 mm thick) with silica gel G (Kieselgel G nach Stahl; E. Merck) were activated at 100° C. for half an hour. The solution containing the isolated substance was applied 1 cm above the edge of the plates were run in an organic solvent mixture of n-butanol, acetic acid and water (12:5:2). The developed plates were dried at room temperature and sprayed with 0.25% nin-hydrin in acetone. The nin-hydrin positive spots (R=0.19) of the isolate corresponding to insulin were collected from about 200 unsprayed plates along with the silica gel G and extracted with 50% ethanol buffered with ammonium hydroxide or 10% formic acid. The extract was filtered and dried in vacuo. Pure colorless crystals thus obtained were weighed (3 g/100 gram dry weight of seeds).

The melting point of the purified compound (232°–235° C.) as well as the mmp (234° C.) were determined. The melting point of the standard insulin was recorded as 233° C.

The standard sample of insulin as well as the isolated polypeptide-k were hydrolyzed under reflux with 6N HCI for 20 hours separately. The hydrolyzes were filtered, dried, reconstituted separately in 50% ethanol and applied on strips of Whatman No. 1 paper. The paper strips were run in an organic solvent mixture of n-butanol, acetic acid and water (5:1:1). The hydrolyzate of both the isolated and the standard insulin were also applied separately along with the known amino acids (hydroxylysine, methionine, a hydroxyproline and trytophan). The various developed chromatograms were sprayed with 0.25% nin-hydrin in acetone. The amino acids of the hydrolyzate of the standard nearly coincided exactly with those of the hydrolyzate of the isolated compound except glutamine being extra amino acid in isolated polypeptide-k. Hydroxylysine, hydroxy-proline and tryptophan were found to be absent from the hydrolyzate of the isolated polypeptide-k as well as of the standard hydrolyzate which gave an indication that the isolated polypeptide-k is nearly identical with that of the insulin. The polypeptide-k showed 18 amino acids. Continuation of polypeptide-k with Diaonil was found to be the best. The polypeptide-k comprising 18 amino acids as shown in Table 2 here below:

TABLE 2

| Amino acid | aaa936 | Avg nmoles | μ grams | mole percent | # residues |
|---|---|---|---|---|---|
| Cysac | | | | | |
| Cmcys | | | | | |
| Asx | 3.6346 | 3.635 | 0.418 | 9.4% | 15.0 |
| Thr | 1.1549 | 1.155 | 0.117 | 3.0% | 4.8 |
| Ser | 2.0456 | 2.046 | 0.178 | 5.3% | 8.5 |
| Glx | 6.6195 | 6.619 | 0.848 | 17.1% | 27.4 |
| pro + cys | (2.1133) | (2.113) | (0.205) | 5.5% | (8.7) |
| Gly | 3.4509 | 3.451 | 0.197 | 8.9% | 14.3 |
| Ala | 2.8168 | 2.817 | 0.200 | 7.3% | 11.6 |
| Val | 2.6160 | 2.616 | 0.259 | 6.8% | 10.8 |
| Met | 0.5625 | 0.563 | 0.074 | 1.5% | 2.3 |
| Ileu | 1.8404 | 1.840 | 0.208 | 4.8% | 7.6 |
| Leu | 3.1701 | 3.170 | 0.359 | 8.2% | 13.1 |
| Tyr | 1.0645 | 1.064 | 0.174 | 2.7% | 4.4 |
| Phe | 1.6115 | 1.612 | 0.237 | 4.2% | 6.7 |
| His | (1.2110) | (1.211) | (0.166) | 3.1% | (5.0) |
| Lys | | | | | |
| Trp | (not determined) | | | | |
| Arg | 3.5602 | 3.560 | 0.556 | 9.2% | 14.7 |

% injected 100%
total residues: 160

Disc electrophoresis was carried out (10% SDS Biophore Gel, run in tris buffer, operating pH 6.1, 3% acetic acid in lower cell; 90 V, mA 2.5 per tube; Bromophenol blue tracking dye). Samples of the crystallized isolate and bovine containing dithiothreltol and EDTA, injected and run for 7 hr. Gel collected from the tubes were stained (0.05% coomassie Brilliant Blue R-250 in 7% aqueous acetic acid) and washed with 10% acetic acid. Electrophoretic pattern of both the isolate and the bovine insulin were nearly identical as shown in FIG. 2 of the accompanying drawings. FIGS. 3(*a*) to (*d*) show the results of the disc electrophoresis which show that the proteins move as a single main peak. The sequence of the amino acids in polypeptide-k is shown in FIG. 4. Immuno-assays of polypeptide-k did not show any cross reaction when tested with bovine insulin.

Below are representative examples of case studies, wherein patients have been administered the hypoglyceamic composition of the invention. All these patients were afflicted with diabetes mellitus, though the chronicity varied from case to case. The patients were advised to consume good quality food substantially free from starch, and containing at least 1 fruit. The patients were also advised exercise besides use of the composition of the invention. Most of the patients took drugs like Diaonil/Glyciphase/Glynase/DBI/Euglucon/Dimicron or combination of glyciphage and glynase before commencement of the treatment.

Gradual fall in blood sugar level of the patients was observed after one week to 40 days and then it came to normal. Continued intake of the composition of the invention varied from 6 months to 3 years as four doses 10–15 minutes before each meal sublingually. In patients with blood sugar level from 355 or more Diaonil in doses of 2 (1+1) or 1 (½+½) was supplemented with the dose of the composition (morning, evening). Diaonil was withdrawn completely after 15 days.

Case Studies

1. Mr. Vivek Mukherjee, aged 18, complained of leg pain, excessive thirst for water, frequent urination and blurring vision. Upon examination, his blood sugar level was found to be 425 mg/dl as pp and fasting as 209 mg/dl. No oral drug worked effectively. The patient was advised to consume the hypoglycaemic composition of the invention (12 mg/dl/dose and 4 doses per day. Each dose was consumed 10 minutes before every meal without any liquid or solid) along with diaonil (1+1+1). This reduced the blood sugar level considerably. Diaonil was reduced to half after one month and later withdrawn completely and surprisingly the blood sugar level was reduced to 114 mg/dl (pp) after 2 months. The patient is now completely dependant on the composition of the invention and is maintaining normal blood sugar level with no side effects.

2. Another patient, Prof. K. P. Mishra, aged 71 years, was a chronic diabetic with a blood sugar level of 305 mg/dl. He was on insulin (18 units/day). The patient was advised to consume the composition of the invention 4 times. He is maintaining normal blood sugar for the last two years.

3. Mr. D. P. Gaur, aged 60 years, was a chronic diabetic since last 10 years. He developed neuropathy and lethargicity in the body even on taking 60 units of insulin. There were symptoms of high blood pressure and high triglyceride levels. This patient started taking the composition of the invention 4 times a day alongwith the insulin which was reduced. The blood sugar level was reduced. The insulin dose was gradually reduced and finally withdrawn and now the patient is maintaining normal blood sugar level and keeping fit with 4 doses of compositions of invention.

4. Mrs. Rashmi Geha, 46 years old, developed symptoms, which on examination of blood profile confirmed (haemoglobin-glycosilation test) the diabetes (320 mg/dl). She started taking the powder of the invention and has been maintaining normal blood sugar levels She has not taken any other oral drug.

5. Mr. Banerjee, 70 years old, was a chronic patient (15–20 years) and with a high blood pressure, high triglyceride and cholesterol levels. He took the powder for 3 years, four doses per day of composition of the invention. This kept normal blood sugar levels and controlled levels of blood pressure and cholesterol levels.

TABLE 3

Effect of Gourdin (polypeptide-k) on blood sugar level in patients with diabetes mellitus.

| No. of subjects | Diabetes duration (yrs.) | +Range of blood sugar level mg/dl (post prantl) | *Polypeptide-k effect Mean mg/dl fall in blood sugar level (after 207 days). |
|---|---|---|---|
| 250 | 2–5 | 160–200 | 120–110 |
| 250 | 6–10 | 210–350 | 150–190 |
| 100 | 11–15 | 355–450 | 250–270 |
| 5 | 15–20 | 460–500 | 282 |

The Applicant observed that the present novel Polypeptide-k is highly effective as compared to Polypeptide-p due to its stable nature. It works miracle when used along with Diaonil and it brings the high blood sugar level above 250 mg/dl or above to normal with in 2–3 days. It not only reduces the high blood sugar level but also controls the high blood pressure, by controlling the total cholesterol, HDL, LDL, VLDL and triglycerides. It also takes care of neuropathy and makes the patient feel normal. Side effects in Diabetics are taken care of by polypeptide-k. It also increases the immunity in the patients against the diseases and hence is helping HIV patients also. It has no cross-reaction with insulin. In many patients, the insulin has been withdrawn gradually.

Many patients suffering from diabetics when treated with polypeptide-k showed excellent results in the age group of 50–60 year or above. The patients in the above age group feel normal and full of health. The blood sugar level in various cases has shown 50–55% lowering effect after administration of polypeptide-k and when compared with polypeptide-p, such effect was observed to be 25–30% and that too was fluctuating.

In fact, no patient complained of any side effects when treated with polypeptide-k. Diaonil combination with polypeptide-k have shown excellent results. In some cases, the doses of polypeptide-k have to be reduced from 4–3–2 showing that the pancreases in the long run get rejuvenated and hence, it can be concluded that polypeptide-k activates the inactive insulin present in the blood. After all insulin is an enzyme and attachment of a small peptide of polypeptide-k at any point can make the insulin activated.

When the other blood tests were performed, the creatinine, uric acid and blood urea levels were found to be normal in diabetic patients treated with polypeptide-k. Now, a larger population is responding positively internationally.

The most important property of polypeptide-k is that it brings the pH of the body (blood) to 6. If one is feeling giddy or throwing bile, one tablet can regulate the acidity or alkalinity respectively to normal level pH 6 and the person feels just normal and healthy and thus it can control the functioning of liver as well.

By controlling the neuropathy the patient has no nerve problems. Being from a vegetable source it is easily acceptable.

In case of polypeptide-p such a response has not been observed because of the unstable condition of the protein.

The Following are the Advantages

1. The polypeptide-k was found to be more effective than polypeptide-p isolated by the process claimed in earlier patent No. 176040. The extraction procedure for polypeptide-k was improved and made more effective.

2. Polypeptide-k was found to be highly sublingually effective hypoglyceamic drug.

3. The cholesterol level including total cholesterol, HDL, LDL, VLDL and triglyceride go down to normal using this drug as an antidiabetic remedy.

4. Symptoms as leg pain, lethargy did not appear when more than 500 patients of 2–4 years of duration with this drug was treated. This invention as described in the example is merely illustrative in nature and not intended to restrict the scope of the invention.

The Origin of the Hypoglycaemic Composition and Its Effects

1. It is the protein extract of "Karela"/Bittergourd/ *Momordica charantia* L.

2. Combustion point /mp of Gourdin was found to be 234° C.

3. When analyzed with amino acid analyzer the hydrolyzate showed 18 amino acids.

4. A single electrophoretic band was observed which on scanning showed a single main peak of pure Gourdin.

5. Bio-immunoassays of polypeptide-k were found to be negative against insulin.

6. Pharmacological study revealed a significant blood-sugar-lowering.

7. Polypeptide-k is insoluble in water and partially soluble at pH 9.5 and fully in 10% formic acid.

8. It physically can be tested with nin-hydrin which on heating the soluble fraction turned yellow in colour turning purple later.

9. On sequencing the polypeptide fraction, the first terminal was found to be free.

10. The hypoglycaemic composition of the invention activates the inactive insulin present in the blood and hence, it cures the disease, the time factor depends on the chronicity of the illness.

11. If hereditary, a single dose by a normal person acts as preventive dose.

12. If cholesterol level is high, its intake reduces the level.

13. High Triglyceride level is also reduced.

14. Pain and inflammation of the joints is either eliminated or reduced.

15. Its intake gives a feeling of normalcy to the diabetic patient.

16. No other side effects were observed.

What is claimed is:

1. A protein comprising polypeptide-k extracted from *Momordica charantia*, the polypeptide-k comprising 160 amino acid residues, said amino acid residues consisting of aspartic acid, threonine, serine, glutamine, proline, cysteine, glycine, alanine, valine, methionine, isoleucine, leucine, tyrosine, phenylalanine, histidine, lysine, tryptophan and arginine, the following amino acids being present in the polypeptide-k in the following amounts by mole percent:

| | |
|---|---|
| aspartic acid | 9.4% |
| threonine | 3.0% |
| serine | 5.3% |
| glutamine | 17.1% |
| proline and cysteine | 5.5% |
| glycine | 8.9% |
| alanine | 7.3% |
| valine | 6.8% |
| methionine | 1.5% |
| isoleucine | 4.8% |
| leucine | 8.2% |
| tyrosine | 2.7% |
| phenylalanine | 4.2% |
| histidine | 3.1% |
| arginine | 9.2% | said polypeptide-k having the following properties:
  i. being water insoluble but soluble to some extent at pH 9.5 and completely soluble 10% formic acid,
  ii. having a free N-terminal,
  iii. being stable,
  iv. having a shelf-life of about 18 months,
  v. having a combustion point of 234° C., and
  vi. not showing cross reaction when tested with bovine insulin.

* * * * *